(12) United States Patent
Shimizu et al.

(10) Patent No.: US 10,869,829 B1
(45) Date of Patent: Dec. 22, 2020

(54) COMPOSITION CONTAINING MORINGA EXTRACT AND/OR PULVERIZED PRODUCT

(71) Applicants: Kazuo Shimizu, Suzuka (JP); Masamitsu Moriwaki, Suzuka (JP)

(72) Inventors: Kazuo Shimizu, Suzuka (JP); Masamitsu Moriwaki, Suzuka (JP)

(73) Assignee: TAIYO KAGAKU CO., LTD., Yokkaichi (JP)

( * ) Notice: Subject to any disclaimer, the term of this patent is extended or adjusted under 35 U.S.C. 154(b) by 0 days.

(21) Appl. No.: 16/769,625

(22) PCT Filed: Nov. 8, 2019

(86) PCT No.: PCT/JP2019/043940
§ 371 (c)(1),
(2) Date: Jun. 4, 2020

(87) PCT Pub. No.: WO2020/116092
PCT Pub. Date: Jun. 11, 2020

(30) Foreign Application Priority Data

Dec. 7, 2018 (JP) ................. 2018-229933

(51) Int. Cl.
*A61K 36/00* (2006.01)
*A61K 8/9789* (2017.01)
*A23L 33/105* (2016.01)

(52) U.S. Cl.
CPC .......... *A61K 8/9789* (2017.08); *A23L 33/105* (2016.08); *A23V 2002/00* (2013.01)

(58) Field of Classification Search
None
See application file for complete search history.

(56) References Cited

U.S. PATENT DOCUMENTS

2018/0318367 A1  11/2018  Sugiura et al.

FOREIGN PATENT DOCUMENTS

| JP | 4032393 B2 | 11/2007 |
| JP | 2008-237117 A | 10/2008 |
| JP | 2012-60995 A | 3/2012 |
| JP | 2017-217006 A | 12/2017 |
| WO | WO 2017/073473 A1 | 5/2017 |

OTHER PUBLICATIONS

El Sohaimy, S.A., et al. "Biochemical and functional properties of Moringa oleifera leaves and their potential as a functional food," Giobai Advanced Research Journal of Agricultural Science, Apr. 2015, vol. 4, No. 4, pp. 188-199.
Lee, J.G., et al, "The Mechanism of Deterioration of the Glucosinolate-Myrosynase System in Radish Roots During Cold Storage After Harvest," Food Chem., 2017, vol. 233, pp. 60-68.
Waterman, C., et al, "Stable, Water Extractable Isothiocyanates From Moringa Oleifera Leaves Attenuate Inflammation in Vitro," Phytochemistry, 2014, vol. 103, pp. 114-122.

*Primary Examiner* — Qiuwen Mi
(74) *Attorney, Agent, or Firm* — Birch, Stewart, Kolasch & Birch, LLP

(57) ABSTRACT

A composition containing a *Moringa* extract and/or a *Moringa* pulverized product, wherein a mass ratio of a content of a moringin to a content of a glucomoringin (moringin/glucomoringin) is from 0.00005 to 0.30, and wherein a myrosinase is deactivated, or the composition does not contain a myrosinase. The composition of the present invention is useful in the fields of foodstuff, cosmetics, and the like.

3 Claims, 2 Drawing Sheets

COMPOSITION CONTAINING MORINGA EXTRACT AND/OR PULVERIZED PRODUCT

TECHNICAL FIELD

The present invention relates to a composition containing a *Moringa* extract and/or a *Moringa* pulverized product, and foodstuff and cosmetics containing the composition.

BACKGROUND ART

A plant belonging to the genus *Moringa* (also simply referred to herein to as "*Moringa*") is a plant which is widely familiar as a medicinal plant in India, Southeast Asia and the like, and has been found to have various useful physiological functions such as anti-oxidation effects and anti-inflammatory effects. *Moringa* richly contains minerals, amino acids, benzyl glucosinolates (BGLs) and the like as active ingredients for these effects. Recently, a dry pulverized product of leaves or roots of *Moringa*, an extract powder which is extracted with hot water, a water-containing alcohol or the like from the pulverized product as a raw material, and the like have been sold as a raw material of a functional food, and are remarked (see, Patent Publications 1 and 2, and Non-Patent Publication 1).

*Moringa* contains a myrosinase which allows to convert (enzymatically degrade) benzyl glucosinolate to benzyl isothiocyanate (BITC). Benzyl glucosinolate and myrosinase do not react because they are separated and localized in a usual state. However, when subjected to an extraction with a solvent or pulverization, benzyl glucosinolate and myrosinase are vigorously reacted, and benzyl glucosinolate is converted to benzyl isothiocyanate. For this reason, in a *Moringa* extract which is an extract of a *Moringa*, benzyl glucosinolate is no longer present. In view of the above, the applicant of the present application has proposed that a specified pretreatment is carried out to deactivate the myrosinase, thereby inhibiting the degradation of benzyl glucosinolate in the *Moringa* extract, and the like (Patent Publication 3).

PRIOR ART REFERENCES

Patent Publications

Patent Publication 1: Japanese Patent No. 4032393
Patent Publication 2: Japanese Patent Laid-Open No. 2008-237117 Patent Publication 3: Japanese Patent Laid-Open No. 2017-217006

Non-Patent Publications

Non-Patent Publication 1: *Global Advanced Research Journal of Agricultural Science* (ISSN:2315-5094), 4(4), 188-199, April, 2015

SUMMARY OF THE INVENTION

Problems to be Solved by the Invention

The *Moringa* extract of Patent Publication 3 has useful physiological functions and high safety. However, further improvements are in demand for the area under the curve (AUC) of blood concentration-time, which is an index of absorption amount into a body.

An object of the present invention is to provide a composition having useful physiological functions and being excellent in AUC and storage stability, and foodstuff and cosmetics containing the composition.

Means to Solve the Problems

As a result of studying the above problems, it has been found that a composition in which a mass ratio of a content of a moringin, which is one kind of benzyl isothiocyanates, to a content of a glucomoringin, which is one kind of benzyl glucosinolates, is adjusted to a specified range is excellent in AUC. In the benzyl glucosinolates, there are plural analogs in addition to glucomoringin, and the benzyl glucosinolates are a collective name thereof. Therefore, in the present invention, the main active ingredients glucomoringin (4-($\alpha$-L-rhamnosiloxy)benzyl glucosinolate) and its derivative moringin (4-($\alpha$-L-rhamnosiloxy)benzyl isothiocyanate) are used as indices, in place of the benzyl glucosinolates. In addition, in the present invention, it has been found that a composition having excellent storage stability of the glucomoringin is obtained by deactivating or removing a myrosinase. Further, it has been found that a composition having excellent storage stability of a moringin is obtained by allowing the glucomoringin and the moringin to be co-present in the composition of the present invention. The present inventors have made intensive studies on the bases of the findings, and the present invention has been perfected thereby.

The present invention relates to the following [1] to [3]:
[1] A composition containing a *Moringa* extract and/or a *Moringa* pulverized product, wherein a mass ratio of a content of a moringin to a content of a glucomoringin (moringin/glucomoringin) is from 0.00005 to 0.30, and wherein a myrosinase is deactivated, or the composition does not contain a myrosinase.
[2] Foodstuff containing a composition as defined in [1].
[3] Cosmetics containing a composition as defined in [1].

Effects of the Invention

According to the present invention, a composition having useful physiological functions and being excellent in AUC and storage stability, and foodstuff and cosmetics containing the composition can be provided.

MODES FOR CARRYING OUT THE INVENTION

Figure 1:
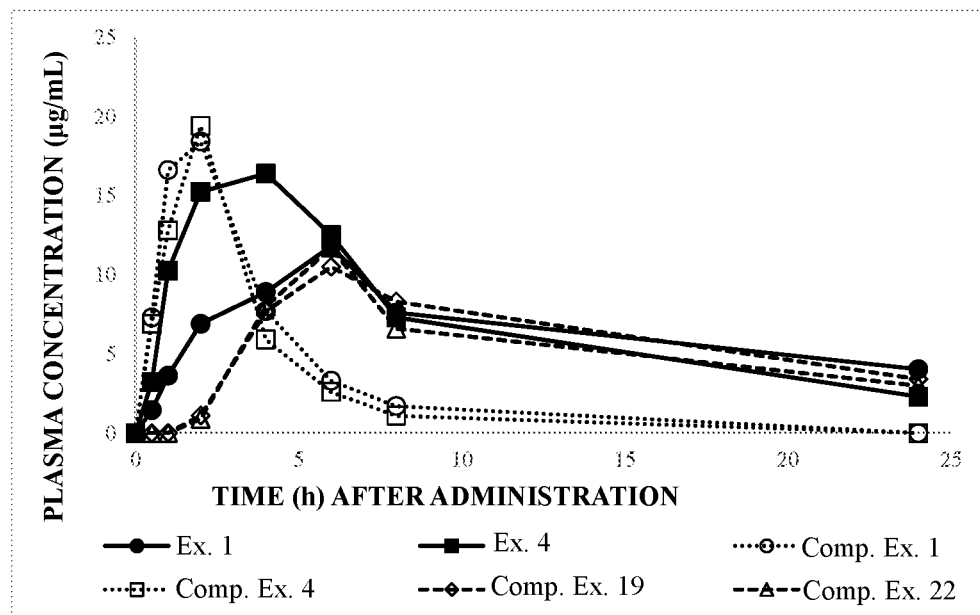
FIG. 1 A graph showing a concentration of a metabolite at each time for Example 1, Example 4, Comparative Example 1, Comparative Example 4, Comparative Example 19, and Comparative Example 22.

The composition of the present invention contains a *Moringa* extract and/or a *Moringa* pulverized product (which may be hereinafter referred to as "a *Moringa* extract or the like"). The *Moringa* extract is obtained by extracting from a *Moringa* with a solvent by a known method. The *Moringa* pulverized product is obtained by pulverizing a *Moringa* with a known pulverizer.

The *Moringa* subjected to the extraction or pulverization includes, but not particularly limited to, for example, *Moringa oleifera, Moringa concanensis, Moringa drouhardii*, and the like. Among them, *Moringa oleifera* is preferred, from the viewpoint that the *Moringa oleifera* is widely cultivated and can be easily harvested. *Moringa oleifera* is a deciduous small arbor which is grown in India in origin, and has other names such as Horseradish tree, Ben nut, *Malungai* (in Tagalog), *Sanjanaa* (in Hindu) and the like.

As parts of a *Moringa* to be extracted or to be pulverized, all of stems, leaves, sheaths (fruit flesh) and seeds can be used. These parts may be used in the raw, or may be used after drying, and it is preferable that these parts are used after drying, from the viewpoint of the storage stability as a raw material and the yield during the production of an extract.

As the solvent used in the extraction, water, an organic solvent, or a mixed solvent of water and an organic solvent is used. The organic solvent includes lower alcohols which can be mixed with water (a monohydric or polyhydric alcohol containing 1 to 4 carbon atoms such as methanol, ethanol, propanol, propylene glycol, butylene glycol, and glycerol), acetone and the like. When the solvent is a mixed solvent of these organic solvents and water, the organic solvents may be previously mixed with water and used, or two or more kinds of the organic solvents may be mixed with water and used. Although a mixing proportion with an organic solvent in the case of the mixed solvent with water can be used from exceeding 0% to less than 100%, extraction only with water is preferred, from the viewpoint of safety. The liquid amount of the solvent used in the extraction is, but not particularly limited to, for example, from 200 to 3,000 parts by mass, based on 100 parts by mass of the *Moringa* to be extracted. The temperature of the solvent during the extraction can be, but not particularly limited to, for example, from 20° to 95° C. The extraction time can be, but not particularly limited to, for example, from 30 to 150 minutes, from the viewpoint of production efficiency. The extraction can be carried out in a state with stirring or a static state. After the extraction, the extract is subjected to a treatment such as filtration or centrifugation to remove the residues, and thereafter an extraction solvent can be removed by depressurization or the like. In addition, the extract can be optionally dried with a spray-drier or the like in a case where an extract is powdered, and the like.

The composition of the present invention contains a glucomoringin and a moringin. It has been known that these components have useful physiological functions such as anti-fatigue, anti-oxidation, nourishment and revitalization and hormonal regulation. However, it has been considered that the effects of various activities are basically owned by the moringin, and that the glucomoringin is an active precursor. It has been known that when a glucomoringin is ingested, the glucomoringin is metabolized by enterobacteria in the bodies, and converted to a moringin. However, a composition containing a *Moringa* extract and/or a *Moringa* pulverized product, the composition containing a glucomoringin and a moringin at a certain ratio has not been known. In addition, the composition of the present invention is a composition in which a myrosinase is deactivated, or the composition does not contain a myrosinase.

The content of the glucomoringin in the composition of the present invention, calculated in terms of a dry solid content, is preferably 1.5% by mass or more, more preferably 6% by mass or more, even more preferably 10% by mass or more, and even more preferably 15% by mass or more, from the viewpoint of exhibiting useful physiological functions. The upper limit can be, but not particularly limited to, for example, 50% by mass or less. The content of the glucomoringin is measured in accordance with a method described in Examples set forth below.

The content of the moringin in the composition of the present invention, calculated in terms of a dry solid content, is preferably 0.0005% by mass or more, more preferably 0.005% by mass or more, even more preferably 0.01% by mass or more, and even more preferably 0.1% by mass or more, from the viewpoint of exhibiting useful physiological functions. The upper limit can be, but not particularly limited to, for example, 15% by mass or less. The content of the moringin is measured in accordance with a method described in Examples set forth below.

The mass ratio of the content of a moringin to the content of a glucomoringin (moringin/glucomoringin) in the composition of the present invention is 0.00005 or more, preferably 0.0002 or more, more preferably 0.002 or more, and even more preferably 0.20 or more, from the viewpoint of AUC, and the mass ratio is 0.30 or less, preferably 0.10 or less, more preferably 0.05 or less, and even more preferably 0.03 or less, from the viewpoint of storage stability. The method of adjusting the mass ratio is not particularly limited, and a *Moringa* extract or the like containing a glucomoringin is mixed with a *Moringa* extract or the like containing a moringin, whereby the composition can be adjusted to any mass ratios. The *Moringa* extract or the like containing a glucomoringin is obtained by deactivating a myrosinase in accordance with a known method, and carrying out extraction. The *Moringa* extract or the like containing a moringin is obtained by carrying out extraction or the like without deactivating a myrosinase, and then deactivating or removing the myrosinase or the like. The means of deactivating or removing a myrosinase includes, for example, a heat treatment at a temperature of 85° C. or higher, an extraction treatment with a solvent having an ethanol content of 80% or more, dialysis, gel filtration, an enzymatic removal treatment by ultrafiltration, and the like. The confirmation of deactivation or removal of the myrosinase can be measured in accordance with a method described in Examples set forth below.

The composition of the present invention can contain free amino acids, and can further contain one or more amino acids selected from the group consisting of, for example, arginine, glutamic acid, alanine, methionine, and cysteine.

The content of the free amino acids in the composition of the present invention is preferably 0.1% by mass or more calculated in terms of a dry solid content of the extract, and more preferably 0.5% by mass or more, from the viewpoint of the health promotion. The upper limit can be, but not particularly limited to, for example, 2.0% by mass or less. When the free amino acids are contained in two or more kinds, the content refers to a total amount thereof.

The composition of the present invention can contain optional ingredients including minerals such as zinc, potassium, calcium, iron, copper, sodium, and magnesium; vitamins such as vitamin A, vitamin B1, vitamin B2, vitamin C, vitamin D, and vitamin E; and excipients such as dextrin, maltodextrin, galactomannan, cyclodextrin, starches, and lactose, and the like.

Since the composition of the present invention has useful physiological functions and is excellent in AUC and storage stability, the composition can be blended in foodstuff and cosmetics.

Since the glucomoringin and the moringin are co-present in the composition of the present invention, in the foodstuff, a bitterness or a color change originated from the glucomoringin can be inhibited, or pungency or an unpleasant odor originated from the moringin can be inhibited. The foodstuff may be, for example, beverages such as refreshing beverages, carbonated beverages, nutritional supplement beverages, fruit beverages, and lactic acid beverages, or concentrated stock solutions or powders for preparing these beverages, or the like. In addition, the composition of the present invention can be added to cold confectioneries such as ice cream, sherbet, or frappe (kaki kori); or noodles such as buckwheat noodles (soba), wheat noodles (udon), fentiao, skin of dumplings stuffed with meat and vegetables, skin of shao-mai, Chinese noodles or instant noodles. Further, the composition of the present invention can be added to confectioneries such as a candy, a chewing gum, a chocolate, a tablet candy, a gummy candy, a snack, a biscuit, a jelly, a custard pudding, a jam, a cream, or a baked confectionery. Also, the composition of the present invention can be added to a marine or livestock processed food such as tubular roll of steamed fish paste, ham, or sausage; a dairy product such as a processed milk or a fermented milk, or the composition can be added to a fat or oil and a fat or oil processed food such as salad oil, tempura oil, margarine, mayonnaise, shortening, whipped cream, and salad dressing; a seasoning such as a sauce or a gravy sauce; a soup, a stew, a salad, a ready-made side dish, a pickle or the like. Moreover, the composition can be added to various forms of health and nutritional supplemental foods in the forms of tablets, capsules, and drinks; other quasi-drugs such as oral cavity refreshing agents that are used in the oral cavity such as oral refreshing agents and oral deodorizing agents, dentifrices, and mouthwashes; emollient creams, emollient lotions, or the like.

The blending amount of the composition of the present invention is not particularly limited, and the composition can be blended in the foodstuff so that the amount is, for example, from 0.01 to 80% by mass, calculated in terms of the dry solid content of the extract.

The cosmetics include, for example, skin care products, makeup products, fragrance products, body care products, hair care products, and the like. As the skin care products, the composition which is added to lotions such as emollients, astringent lotions, cleansing lotions, multi-layered cosmetics; milky lotions such as emollient lotions, moisturizing lotions, milky lotions, nourishing lotions, nourishing milks, skin moisturizers, moisturizing emulsions, massage lotions, cleansing lotions, protect emulsions, sun protect, sun protectors, UV care milk, sunscreens, make-up lotions, keratin smoothers, elbow lotions, hand lotions, and body lotions; creams such as emollient creams, nourishing creams, nutritive creams, varnishing creams, moisturizing creams, night creams, massaging creams, cleansing creams, make-up creams, base skin care creams, pre-make-up creams, sunscreen creams, suntan creams, depilatory creams, deodorant creams, shaving creams, and keratin softening creams; gels such as moisturizing gels; essences such as moisture-retaining essences, whitening essences, and ultraviolet-protecting essences; liposome cosmetics such as liposome cosmetic solutions and liposome lotions; packs and masks such as peel-off packs, powder packs, washing packs, oil packs, and cleansing masks; cleansing agents such as cleansing foams, cleansing creams, cleansing milks, cleansing lotions, cleansing gels, cleansing oils, cleansing masks, cleansing powders, face wash powders; soaps such as toilet soaps, transparent soaps, medicated soaps, liquid soaps, shaving soaps, and synthetic toilet soaps can be used. As the make-up products, the composition which is added to face powders and dusting powders, foundations, lipsticks, lip glosses, cheek rouges, eyeliners, mascaras, eye shadows, eyebrow pencils, eyebrows, nail polishes, polish removers, and nail treatments can be used. As the fragrance products, the composition which is added to colognes, perfumes, parfum, eaux de parfum, eaux de toilette, solid perfumes, fragrance powders, perfumed soaps, body lotions, bath oils, or the like can be used. As the body care products, the composition which is added to body cleansers such as body shampoos; deodorant cosmetics such as deodorant lotions, deodorant powders, deodorant sprays, and deodorant sticks; decolorizers, and depilatory and hair removing agents; bathing agents; insect repellents such as insect repellent sprays can be used. As the hair care products, the composition which is added to shampoos such as oil shampoos, cream shampoos, conditioning shampoos, dandruff shampoos, hair color shampoos, two-in-one conditioning shampoos; rinses, treatments, hair packs, color lotions, split end menders, permanent wave agents, oxidizing dyes, hair bleaches, hair color pretreatments, hair color aftertreatments, permanent pretreatments, permanent after-treatments, hair manicure agents, hair tonics, or hair grow agents can be used.

EXAMPLES

The examples of the present invention will be described hereinbelow, without intending to limit the present invention to these examples. Here, "%" means "% by mass" unless specified otherwise.

Preparation Examples 1 to 44 of *Moringa* Extracts or *Moringa* Pulverized Products

*Moringa* seeds were pulverized with a mill to give a pulverized product of seeds. Five-hundred grams of deionized water (90° C.) was added to 100 g of the pulverized product of seeds, and the mixture was stirred (pre-treated) for 5 minutes. Thereafter, 1,500 g of deionized water (10° C.) was added to the mixture to adjust the temperature to 35° C., and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 10 g of a *Moringa* extract of Preparation Example 1.

The same procedures as in Preparation Example 1 were carried out except that dry *Moringa* leaves were pulverized with a mill, and the pulverized product of leaves obtained was used, to give 15 g of a *Moringa* extract of Preparation Example 2.

The same procedures as in Preparation Example 1 were carried out except that *Moringa* stems were pulverized with a hammer-mill, and the pulverized product of stems obtained was used, to give 10 g of a *Moringa* extract of Preparation Example 3.

The same procedures as in Preparation Example 1 were carried out except that *Moringa* sheaths were cut into 1 cm or so, freeze-dried, and pulverized with a mill, and the dry pulverized product of sheaths obtained was used, to give 10 g of a *Moringa* extract of Preparation Example 4.

In the *Moringa* extracts of Preparation Examples 1 to 4, the myrosinase was deactivated by a pretreatment at 90° C., so that the moringin was not present therein.

*Moringa* seeds were pulverized with a mill to give a pulverized product of seeds. Two-thousand grams of deionized water (90° C.) was added to 100 g of the pulverized product of seeds, and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 15 g of a *Moringa* extract of Preparation Example 5.

The same procedures as in Preparation Example 5 were carried out except that dry *Moringa* leaves were pulverized with a mill, and the pulverized product of leaves obtained was used, to give 20 g of a *Moringa* extract of Preparation Example 6.

The same procedures as in Preparation Example 5 were carried out except that *Moringa* stems were pulverized with a hammer-mill, and the pulverized product of stems obtained was used, to give 20 g of a *Moringa* extract of Preparation Example 7.

The same procedures as in Preparation Example 5 were carried out except that *Moringa* sheaths were cut into 1 cm or so, freeze-dried, and pulverized with a mill, and the dry pulverized product of sheaths obtained was used, to give 18 g of a *Moringa* extract of Preparation Example 8.

In the *Moringa* extracts of Preparation Examples 5 to 8, the myrosinase was deactivated by an extraction treatment at 90° C., so that the moringin was not present therein. In addition, even if a slight amount of moringin was produced by enzymatic decomposition, the moringin would not be present due to thermal degradation.

*Moringa* seeds were pulverized with a mill to give a pulverized product of seeds. Two-thousand grams of a 50% (v/v) aqueous ethanol solution (55° C.) was added to 100 g of the pulverized product of seeds, and the mixture was stirred for 2 hours. Thereafter, the mixture was filtered with a filter paper, and the filtrate was subjected to a ultrafiltration membrane treatment to remove the endogenous myrosinase therein. Thereafter, the treated mixture was concentrated with a rotary evaporator under a reduced pressure. The concentrated solution obtained was dried with a freeze-drier to give 12 g of a *Moringa* extract of Preparation Example 9.

The same procedures as in Preparation Example 9 were carried out except that dry *Moringa* leaves were pulverized with a mill, and the pulverized product of leaves obtained was used, to give 25 g of a *Moringa* extract of Preparation Example 10.

The same procedures as in Preparation Example 9 were carried out except that *Moringa* stems were pulverized with a hammer-mill, and the pulverized product of stems obtained was used, to give 25 g of a *Moringa* extract of Preparation Example 11.

The same procedures as in Preparation Example 9 were carried out except that *Moringa* sheaths were cut into 1 cm or so, freeze-dried, and pulverized with a mill, and the dry pulverized product of sheaths obtained was used, to give 20 g of a *Moringa* extract of Preparation Example 12.

In the *Moringa* extracts of Preparation Examples 9 to 12, the myrosinase could not be deactivated at an ethanol content of 50% or so, so that the *Moringa* extracts have myrosinase activity during the extraction treatment, whereby producing a moringin.

*Moringa* seeds were pulverized with a mill to give a pulverized product of seeds. Two-thousand grams of a 90% (v/v) aqueous ethanol solution (35° C.) was added to 100 g of the pulverized product of seeds, and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 10 g of a *Moringa* extract of Preparation Example 13.

The same procedures as in Preparation Example 13 were carried out except that dry *Moringa* leaves were pulverized with a mill, and the pulverized product of leaves obtained was used, to give 20 g of a *Moringa* extract of Preparation Example 14.

The same procedures as in Preparation Example 13 were carried out except that *Moringa* stems were pulverized with a hammer-mill, and the pulverized product of stems obtained was used, to give 20 g of a *Moringa* extract of Preparation Example 15.

The same procedures as in Preparation Example 13 were carried out except that *Moringa* sheaths were cut into 1 cm or so, freeze-dried, and pulverized with a mill, and the dry pulverized product of sheaths obtained was used, to give 18 g of a *Moringa* extract of Preparation Example 16.

In the *Moringa* extracts of Preparation Examples 13 to 16, the myrosinase was deactivated or the myrosinase was precipitated in the solution by the extraction treatment with a 90% ethanol, thereby inhibiting a contact with the glucomoringin, so that the moringin not present therein.

*Moringa* seeds were pulverized with a mill to give a pulverized product of seeds. One-hundred grams of the pulverized product of seeds was subjected to an autoclave treatment at 121° C. for 20 minutes to give 100 g of a *Moringa* pulverized product of Preparation Example 17.

The same procedures as in Preparation Example 17 were carried out except that dry *Moringa* leaves were pulverized with a mill, and the pulverized product of leaves obtained was used, to give 100 g of a *Moringa* pulverized product of Preparation Example 18.

The same procedures as in Preparation Example 17 were carried out except that *Moringa* stems were pulverized with a hammer-mill, and the pulverized product of stems obtained was used, to give 100 g of a *Moringa* pulverized product of Preparation Example 19.

The same procedures as in Preparation Example 17 were carried out except that *Moringa* sheaths were cut into 1 cm or so, freeze-dried, and pulverized with a mill, and the dry pulverized product of sheaths obtained was used, to give 100 g of a *Moringa* pulverized product of Preparation Example 20.

In the *Moringa* pulverized products of Preparation Examples 17 to 20, the myrosinase was deactivated by the autoclave treatment at 121° C., and the moringin was also not present due to thermal decomposition.

*Moringa* seeds were pulverized with a mill to give a pulverized product of seeds. Two-thousand grams of deionized water (55° C.) was added to 100 g of the pulverized product of seeds, and the mixture was stirred for 1 hour. Thereafter, the mixture was filtered with a filter paper, and subjected to a ultrafiltration membrane treatment to remove the endogenous myrosinase. Thereafter, the treated mixture was concentrated with a rotary evaporator under a reduced pressure. The concentrated solution obtained was dried with a freeze-drier to give 15 g of a *Moringa* extract of Preparation Example 21.

The same procedures as in Preparation Example 21 were carried out except that dry *Moringa* leaves were pulverized with a mill, and the pulverized product of leaves obtained was used, to give 20 g of a *Moringa* extract of Preparation Example 22.

The same procedures as in Preparation Example 21 were carried out except that *Moringa* stems were pulverized with a hammer-mill, and the pulverized product of stems obtained was used, to give 20 g of a *Moringa* extract of Preparation Example 23.

The same procedures as in Preparation Example 21 were carried out except that *Moringa* sheaths were cut into 1 cm or so, freeze-dried, and pulverized with a mill, and the dry pulverized product of sheaths obtained was used, to give 18 g of a *Moringa* extract of Preparation Example 24.

In the *Moringa* extracts of Preparation Examples 21 to 24, the *Moringa* extracts have myrosinase activity during the extraction treatment, whereby a moringin was produced.

*Moringa* seeds were pulverized with a mill to give a pulverized product of seeds. Two-thousand grams of a 50% (v/v) aqueous ethanol solution (75° C.) was added to 100 g of the pulverized product of seeds, and the mixture was stirred for 2 hours. Thereafter, the mixture was filtered with a filter paper, and the filtrate was subjected to a ultrafiltration membrane treatment to remove the endogenous myrosinase. Thereafter, the treated mixture was concentrated with a rotary evaporator under a reduced pressure. The concentrated solution obtained was dried with a freeze-drier to give 12 g of a *Moringa* extract of Preparation Example 25.

The same procedures as in Preparation Example 25 were carried out except that dry *Moringa* leaves were pulverized with a mill, and the pulverized product of leaves obtained was used, to give 25 g of a *Moringa* extract of Preparation Example 26.

The same procedures as in Preparation Example 25 were carried out except that *Moringa* stems were pulverized with a hammer-mill, and the pulverized product of stems obtained was used, to give 25 g of a *Moringa* extract of Preparation Example 27.

The same procedures as in Preparation Example 25 were carried out except that *Moringa* sheaths were cut into 1 cm or so, freeze-dried, and pulverized with a mill, and the dry pulverized product of sheaths obtained was used, to give 20 g of a *Moringa* extract of Preparation Example 28.

In the *Moringa* extracts of Preparation Examples 25 to 28, the myrosinase could not be deactivated at an ethanol content of 50% or so, and the myrosinase activity was enhanced at an extraction temperature of 75° C., so that the glucomoringin was not present.

*Moringa* seeds were pulverized with a mill to give a pulverized product of seeds. One-hundred grams of deionized water (25° C.) was added to 100 g of the pulverized product of seeds, and the mixture was stirred (pre-treated). Thereafter, the stirred mixture was allowed to stand at 55° C. for 4 hours. The mixture obtained was further dried at 90° C. for 1 hour, to deactivate the endogenous myrosinase to give 100 g of a *Moringa* pulverized product of Preparation Example 29.

The same procedures as in Preparation Example 29 were carried out except that dry *Moringa* leaves were pulverized with a mill, and the pulverized product of leaves obtained was used, to give 100 g of a *Moringa* pulverized product of Preparation Example 30.

The same procedures as in Preparation Example 29 were carried out except that *Moringa* stems were pulverized with a hammer-mill, and the pulverized product of stems obtained was used, to give 100 g of a *Moringa* pulverized product of Preparation Example 31.

The same procedures as in Preparation Example 29 were carried out except that *Moringa* sheaths were cut into 1 cm or so, freeze-dried, and pulverized with a mill, and the dry pulverized product of sheaths obtained was used, to give 100 g of a *Moringa* pulverized product of Preparation Example 32.

In the *Moringa* pulverized products of Preparation Examples 29 to 32, the *Moringa* pulverized products have myrosinase activity when allowed to stand at 55° C., so that a moringin was produced.

The same procedures as in Preparation Examples 21 to 32 were carried out except that the treatment of deactivation or removal of the myrosinase was not carried out to give *Moringa* extracts or *Moringa* pulverized products of Preparation Examples 33 to 44.

The content of the glucomoringin and the content of the moringin in the *Moringa* extracts or the *Moringa* pulverized products of Preparation Examples 1 to 32 are shown in Table 1. Here, the content of the glucomoringin or the content of the moringin of the *Moringa* extracts or the *Moringa* pulverized products of Preparation Examples 33 to 44 were the same as those of Preparation Examples 21 to 32.

Contents of Glucomoringin and Moringin

The content of the glucomoringin (calculated in terms of a dry solid content) and the content of the moringin (calculated in terms of a dry solid content) of the *Moringa* extract or the *Moringa* pulverized product of each of Preparation Examples were analyzed on the bases of the following conditions. The results are shown in Table 1. Here, the contents of the glucomoringin and the moringin in the composition of the present invention can also be measured by using HPLC. The preparation of a sample solution is not particularly limited. Water, an organic solvent, or a mixed solvent of water and an organic solvent is optionally added thereto in a proper amount so as to have a concentration suitable for the analyses of the glucomoringin and the moringin, and a solution fraction is collected, to give a sample preparation. The mixing proportion of the organic solvent when used as a mixed solvent with water of exceeding 0% to less than 100% can be used.

The aqueous solution of the *Moringa* extract or the *Moringa* pulverized product of each Preparation Example (solid content concentration: 5.0% (w/v)) was prepared. Three-hundred microliters of acetonitrile was added to 100 μL of these sample solutions and mixed, and the mixture was filtered. Thereafter, the filtrate was quantitatively analyzed by reversed phase high-performance liquid chromatography under the following conditions:

HPLC (SHIMADZU) analysis: A glucomoringin concentration was calculated by comparing a peak area obtained under the conditions for HPLC of a column: Inertsil HILIC SIZE 4.6 mm×250 mm (GL Science), an eluate A: acetonitrile (93%), an eluate B: 10 mM ammonium formate (7%), a flow rate: 1.0 mL/min, a column temperature in ° C.: 30° C., a wavelength: 220 nm, with a calibration curve of a standard reagent (reagent glucomoringin: EXTRASYNTHESE) to calculate a content of a glucomoringin in each of Preparation Examples. In addition, as to the moringin, peaks of the moringin were identified from molecular weight measurements with a standard reagent (reagent moringin: Chem Faces) and LC-MS, and the content of a moringin was expressed as a converted value using the calibration curve for the glucomoringin. Specifically, the calculation was made as follows.

Moringin: A converted value of a moringin was calculated by comparing the peak area according to the HPLC analysis (carried out under the same conditions as the glucomoringin concentration analysis) with the peak area of the calibration curve of the reagent glucomoringin as follows. Conversion formula to the peak area of a glucomoringin: A/0.738, wherein A is the peak area of a moringin.

Here, when a reagent glucomoringin was completely degraded by a commercially available myrosinase to convert to a moringin, the above formula is used because it could be seen that a value obtained by dividing the peak area of the moringin by a factor of 0.738 can be used in the conversion of the peak area of each component.

B: a converted content of a glucomoringin calculated above (converted in dry solid content basis)

Content of a moringin (converted in dry solid content basis): B×311/570, wherein 311 is a molecular weight of the moringin, and 570 is a molecular weight of the glucomoringin.

As mentioned above, the content of the moringin was converted by multiplying a value calculated once as a glucomoringin by a ratio of the molecular weights.

Confirmation Method for Deactivation or Removal of Myrosinase

An aqueous solution of a *Moringa* extract or a *Moringa* pulverized product (solid content concentration: 5.0% (w/v)) of each of Preparation Examples was prepared. Each of these sample solutions was heated in a water bath at 55° C., and samples were taken after 0 hours and after 20 hours to calculate the contents of a glucomoringin and a moringin. As the confirmation method, it is defined that a myrosinase is deactivated or removed in a case where a decrease in the content of a glucomoringin is not found and an increase in the content of a moringin is not found when the sample solutions after 0 hours and after 20 hours are compared. The phrase "a decrease in the content of a glucomoringin is not found" refers to a content of a glucomoringin in a sample solution after 20 hours of 80% or more, preferably 90% or more, and more preferably 95% or more, in a case where a content of a glucomoringin in a sample solution after 0 hours is defined as 100%. The phrase "an increase in the content of a moringin is not found" refers to a content of a moringin in a sample solution after 20 hours of 120% or less, preferably 110% or less, and more preferably 105% or less, in a case where a content of a moringin in a sample solution after 0 hours is defined as 100%. Here, in Preparation Examples 12 and 21 to 44 not containing a glucomoringin, a glucomoringin was added in a proper amount to examine the presence or absence of an increase or decrease thereof. As a result, it was confirmed that a myrosinase was deactivated or removed in Preparation Examples 1 to 32, and a myrosinase had activity in Preparation Examples 33 to 44. The activity of a myrosinase in the composition of the present invention can be confirmed by an increase or decrease in the contents of a glucomoringin and a moringin in the same manner. The preparation of the sample solutions is not particularly limited. Water, an organic solvent, or a mixed solvent of water and an organic solvent is optionally properly added thereto so as to have a concentration suitable for the analyses of a glucomoringin and a moringin, and a solution fraction is collected, to give a sample solution. A mixing proportion when used as a mixed solvent of the organic solvent with water of exceeding 0% to less than 100% can be practically used.

TABLE 1

| | Raw Materials | Pretreatment | Solvent, Apparatus | Treatment Temp. and Time | Content of Glucomoringin, % by mass | Content of Moringin, % by mass |
|---|---|---|---|---|---|---|
| Extract | | | | | | |
| Prep. Ex. 1 | Seeds | 90° C., 5 min. | Water | 35° C., 2 hours | 16.3 | N. D. |
| Prep. Ex. 2 | Leaves | 90° C., 5 min. | Water | 35° C., 2 hours | 8.2 | N. D. |
| Prep. Ex. 3 | Stems | 90° C., 5 min. | Water | 35° C., 2 hours | 6.3 | N. D. |
| Prep. Ex. 4 | Sheaths | 90° C., 5 min. | Water | 35° C., 2 hours | 7.8 | N. D. |
| Prep. Ex. 5 | Seeds | None | Water | 90° C., 2 hours | 5.2 | N. D. |
| Prep. Ex. 6 | Leaves | None | Water | 90° C., 2 hours | 2.5 | N. D. |
| Prep. Ex. 7 | Stems | None | Water | 90° C., 2 hours | 2.3 | N. D. |
| Prep. Ex. 8 | Sheaths | None | Water | 90° C., 2 hours | 3.6 | N. D. |
| Prep. Ex. 9 | Seeds | None | 50% Ethanol | 55° C., 2 hours | 1.2 | 4.3 |
| Prep. Ex. 10 | Leaves | None | 50% Ethanol | 55° C., 2 hours | 0.3 | 1.9 |
| Prep. Ex. 11 | Stems | None | 50% Ethanol | 55° C., 2 hours | 0.5 | 1.3 |
| Prep. Ex. 12 | Sheaths | None | 50% Ethanol | 55° C., 2 hours | N.D. | 1.6 |
| Prep. Ex. 13 | Seeds | None | 90% Ethanol | 35° C., 2 hours | 14.3 | N. D. |
| Prep. Ex. 14 | Leaves | None | 90% Ethanol | 35° C., 2 hours | 6.8 | N. D. |
| Prep. Ex. 15 | Stems | None | 90% Ethanol | 35° C., 2 hours | 5.4 | N. D. |
| Prep. Ex. 16 | Sheaths | None | 90% Ethanol | 35° C., 2 hours | 6.2 | N. D. |
| Pulverized Product | | | | | | |
| Prep. Ex. 17 | Seeds | None | Autoclaving | 121° C., 20 min. | 5.1 | N. D. |
| Prep. Ex. 18 | Leaves | None | Autoclaving | 121° C., 20 min. | 33 | N. D. |
| Prep. Ex. 19 | Stems | None | Autoclaving | 121° C., 20 min. | 2.9 | N. D. |
| Prep. Ex. 20 | Sheaths | None | Autoclaving | 121° C., 20 min. | 3.1 | N. D. |
| Extract | | | | | | |
| Prep. Ex. 21 | Seeds | None | Water | 55° C., 1 hour | N. D. | 5.1 |
| Prep. Ex. 22 | Leaves | None | Water | 55° C., 1 hour | N. D. | 2.3 |
| Prep. Ex. 23 | Stems | None | Water | 55° C., 1 hour | N. D. | 1.7 |
| Prep. Ex. 24 | Sheaths | None | Water | 55° C., 1 hour | N. D. | 1.9 |
| Prep. Ex. 25 | Seeds | None | 50% Ethanol | 75° C., 2 hours | N. D. | 3.3 |
| Prep. Ex. 26 | Leaves | None | 50% Ethanol | 75° C., 2 hours | N. D. | 1.3 |
| Prep. Ex. 27 | Stems | None | 50% Ethanol | 75° C., 2 hours | N. D. | 1.0 |
| Prep. Ex. 28 | Sheaths | None | 50% Ethanol | 75° C., 2 hours | N. D. | 1.0 |

TABLE 1-continued

Table 1

| | Raw Materials | Pretreatment | Solvent, Apparatus | Treatment Temp. and Time | Content of Gluco-moringin, % by mass | Content of Moringin, % by mass |
|---|---|---|---|---|---|---|
| Pulverized Product | | | | | | |
| Prep. Ex. 29 | Seeds | Add water in amount equivolume to 3 times the amount | Water | Treating at 55° C. for 4 hours, and then drying at 90° C. for 1 hour | N. D. | 1.2 |
| Prep. Ex. 30 | Leaves | | Water | | N. D. | 0.8 |
| Prep. Ex. 31 | Stems | | Water | | N. D. | 0.7 |
| Prep. Ex. 32 | Sheaths | | Water | | N. D. | 0.8 |

Examples 1 to 9 and Comparative Examples 1 to 26

A composition of each of Examples and Comparative Examples was prepared in a mixing proportion as listed in Table 2. As to the compositions only composed of a preparation example in which a myrosinase was deactivated or removed, the enzyme activity was listed in Table 2 as "absence," and as to the compositions containing a *Moringa* extract or a *Moringa* pulverization product of Preparation Examples 33 to 36 and 41 to 44 having a myrosinase activity, the enzyme activity was listed in Table 2 as "presence."

TABLE 2

Table 2

| | Raw Materials | Mixing Proportion, % | Content of Glucomoringin, % by mass | Content of Moringin, % by mass | Moringin/ Glucomoringin | Presence or Absence of Enzyme Activity |
|---|---|---|---|---|---|---|
| Ex. 1 | Seeds | ①99.9:㉑ 0.1 | 16.3 | 0.01 | 0.00031 | Absence |
| Ex. 2 | Leaves | ②95:㉒ 5 | 7.8 | 0.1 | 0.01471 | Absence |
| Ex. 3 | Stems | ③80:㉓ 20 | 5.0 | 0.3 | 0.06712 | Absence |
| Ex. 4 | Sheaths | ④45:㉔ 55 | 3.5 | 1.0 | 0.29068 | Absence |
| Ex. 5 | Seeds | ⑰99.9:㉙ 0.1 | 5.1 | 0.001 | 0.00024 | Absence |
| Ex. 6 | Leaves | ⑱90:㉚ 10 | 3.0 | 0.1 | 0.02572 | Absence |
| Ex. 7 | Stems | ⑲75:㉛ 25 | 2.2 | 0.2 | 0.08153 | Absence |
| Ex. 8 | Sheaths | ⑳50:㉜ 50 | 1.6 | 0.4 | 0.24641 | Absence |
| Ex. 9 | Seeds | ①99.9:㉙ 0.1 | 16.3 | 0.001 | 0.00007 | Absence |
| Comp. Ex. 1 | Seeds | ⑨ 100 | 1.2 | 4.3 | 3.54649 | Absence |
| Comp. Ex. 2 | Leaves | ⑩ 100 | 0.3 | 1.9 | 6.36550 | Absence |
| Comp. Ex. 3 | Stems | ⑪ 100 | 0.5 | 1.3 | 2.61895 | Absence |
| Comp. Ex. 4 | Sheaths | ⑫ 100 | N.D. | 1.6 | — | Absence |
| Comp. Ex. 5 | Seeds | ⑰40:㉙ 60 | 2.0 | 0.7 | 0.35304 | Absence |
| Comp. Ex. 6 | Leaves | ⑱25:㉚ 75 | 0.8 | 0.6 | 0.69442 | Absence |
| Comp. Ex. 7 | Stems | ⑲20:㉛ 80 | 0.6 | 0.6 | 0.97834 | Absence |
| Comp. Ex. 8 | Sheaths | ⑳5:㉜ 95 | 0.2 | 0.7 | 4.68172 | Absence |
| Comp. Ex. 9 | Seeds | ①0.5:㉙ 99.5 | 0.0 | 1.2 | 66.35273 | Absence |
| Comp. Ex. 10 | Seeds | ①99.9:㉝ 0.1 | 16.3 | 0.0 | 0.00031 | Presence |
| Comp. Ex. 11 | Leaves | ②95:㉞ 5 | 7.8 | 0.1 | 0.01471 | Presence |
| Comp. Ex. 12 | Stems | ③80:㉟ 20 | 5.0 | 0.3 | 0.06712 | Presence |
| Comp. Ex. 13 | Sheaths | ④45:㊱ 55 | 3.5 | 1.0 | 0.29068 | Presence |
| Comp. Ex. 14 | Seeds | ⑰99.9:㊶ 0.1 | 5.1 | 0.001 | 0.00024 | Presence |
| Comp. Ex. 15 | Leaves | ⑱90:㊷ 10 | 3.0 | 0.1 | 0.02572 | Presence |
| Comp. Ex. 16 | Stems | ⑲75:㊸ 25 | 2.2 | 0.2 | 0.08153 | Presence |
| Comp. Ex. 17 | Sheaths | ⑳50:㊹ 50 | 1.6 | 0.4 | 0.24641 | Presence |
| Comp. Ex. 18 | Seeds | ①99.9:㊶ 0.1 | 16.3 | 0.001 | 0.00007 | Presence |
| Comp. Ex. 19 | Seeds | ① 100 | 16.3 | N.D. | 0.00000 | Absence |
| Comp. Ex. 20 | Leaves | ② 100 | 8.2 | N.D. | 0.00000 | Absence |
| Comp. Ex. 21 | Stems | ③ 100 | 6.3 | N.D. | 0.00000 | Absence |
| Comp. Ex. 22 | Sheaths | ④ 100 | 7.8 | N.D. | 0.00000 | Absence |
| Comp. Ex. 23 | Seeds | ⑰ 100 | 5.1 | N.D. | 0.00000 | Absence |
| Comp. Ex. 24 | Leaves | ⑱ 100 | 3.3 | N.D. | 0.00000 | Absence |
| Comp. Ex. 25 | Stems | ⑲ 100 | 2.9 | N.D. | 0.00000 | Absence |
| Comp. Ex. 26 | Sheaths | ⑳ 100 | 3.1 | N.D. | 0.00000 | Absence |

*①  to ㊹: Preparation Examples 1 to 44

Confirmation Test for Body Absorption and Metabolism

Nine-week old male SD rats (n=10) were bred at room temperature of 23°±2° C., feeding with a standard feed and water for a week to allow conditioning. The rats were fasted for 18 hours. Thereafter, each of Examples 1 and 4, and Comparative Examples 1, 4, 19, and 22 was dissolved so as to have the same amount in terms of a glucomoringin concentration, and the rats were forcibly orally administered with the solution in an amount of a glucomoringin 30 mg/kg body weight. Here, on the basis of the moringin contained in each of Examples and each of Comparative Examples at dissolving, the content of converted glucomoringin was calculated using the conversion formula of a moringin to a glucomoringin shown in the above analytical conditions, and the concentration was adjusted in terms of the content of a glucomoringin. Plasmas were collected after 0, 0.5, 1, 2, 4, 6, 8, and 24 hours, the metabolite concentration of a glucomoringin was measured in accordance with HPLC method, and AUC was calculated. The results are shown in FIGS. 1 and 2.

Figure 2:
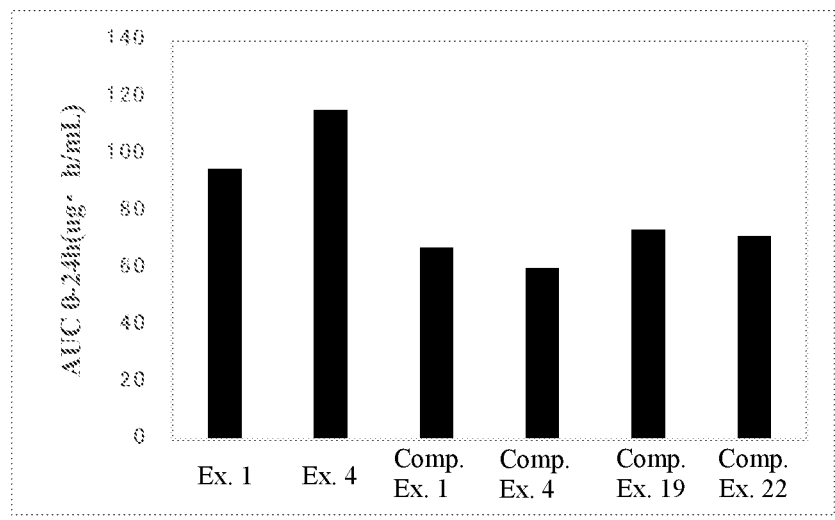
FIG. 2 A graph showing AUC for Example 1, Example 4, Comparative Example 1, Comparative Example 4, Comparative Example 19, and Comparative Example 22.

It can be seen from FIGS. 1 and 2 that the compositions of Examples 1 and 4 show an increase in AUC, as compared to the compositions of Comparative Examples 1, 4, 19, and 22.

Analysis of Blood Glucomoringin Metabolite

Twenty-five microliters of 0.2% phosphoric acid and 200 μL of methanol were added to 100 μL of the plasmas obtained and mixed, and the mixture was centrifuged at 10,000 rpm at 4° C. for 5 minutes to obtain the supernatant. The supernatant obtained was diluted with a phosphate buffer (pH 8.5), 1,2-benzenedithiol was added to the dilution, and the mixture was treated at 65° C. for 2 hours. A product (1,3-benzenedithiol-2-thione) contained in the treated mixture was subjected to quantitative analysis in accordance with reverse phase high-performance liquid chromatography under the following conditions:

HPLC (SHIMADZU) analysis: (Conditions for HPLC: a column: L-column ODS SIZE 4.6 mm×250 mm (CERT), an eluate: water/methanol (20/80,v/v), a flow rate: 0.5 mL/min, a column temperature in ° C.: 30° C., and a wavelength: 365 nm Confirmation of Stability in Moringin A composition of Examples 2, 3, 5, 6, 7, 8, and 9 and Comparative Examples 2, 3, 5, 6, 7, 8, and 9 was each placed in an aluminum bag, and stored at 55° C., and at the same time the sample was taken out of the bag at every given period to measure the content of a moringin. The results are shown in Table 3. It was expressed in terms of a residual rate, %, when an initial content of a moringin is defined as 100%.

TABLE 3

Table 3
Residual Rate of Glucomoringin, %

| Storage Period, Weeks | Ex. 2 | Ex. 3 | Ex. 5 | Ex. 6 | Ex. 7 | Ex. 8 | Ex. 9 | Comp. Ex. 2 | Comp. Ex. 3 | Comp. Ex. 5 | Comp. Ex. 6 | Comp. Ex. 7 | Comp. Ex. 8 | Comp. Ex. 9 |
|---|---|---|---|---|---|---|---|---|---|---|---|---|---|---|
| 0 | 100 | 100 | 100 | 100 | 100 | 100 | 100 | 100 | 100 | 100 | 100 | 100 | 100 | 100 |
| 5 | 89.8 | 87.8 | 89.8 | 91.3 | 90.7 | 88.6 | 94.3 | 64.1 | 67 | 43.3 | 50.1 | 48.3 | 41.1 | 28.3 |
| 4 | 84.1 | 83.7 | 84.6 | 88.3 | 88 | 83.2 | 90.2 | 24.1 | 25 | 11.7 | 18.1 | 17.2 | 10.8 | 4.2 |
| 24 | 28.9 | 27.1 | 31.3 | 37.2 | 33.1 | 28.4 | 44.2 | N.D. | N.D. | N.D. | N.D. | N.D. | N.D. | N.D. |

It can be seen from Table 3 that the compositions of Example 2, 3, 5, 6, 7, 8, and 9 have higher stability in a moringin, as compared to the compositions of Comparative Examples 2, 3, 5, 6, 7, 8, and 9.

Confirmation of Stability in Glucomoringin

An aqueous solution of the compositions of Examples 1 to 9 and Comparative Examples 10 to 18 (concentration: 5.0% (w/v)) was each prepared. The aqueous solution obtained was stored at 25° C., and at the same time the sample was collected at every given period, and the content of a glucomoringin was measured. The results are shown in Table 4. It was expressed in terms of a residual rate, %, when an initial content of a glucomoringin is defined as 100%.

TABLE 4

Table 4
Residual Rate of Glucomoringin, %

| Storage Time, h | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| 0 | 100 | 100 | 100 | 100 | 100 | 100 | 100 | 100 | 100 |
| 1 | 100 | 100 | 100 | 100 | 100 | 100 | 100 | 100 | 100 |
| 2 | 100 | 100 | 100 | 100 | 100 | 100 | 100 | 100 | 100 |
| 5 | 100 | 100 | 100 | 100 | 100 | 100 | 100 | 100 | 100 |
| 24 | 100 | 100 | 100 | 100 | 100 | 100 | 100 | 100 | 100 |

TABLE 4-continued

Table 4
Residual Rate of Glucomoringin, %

| Storage Time, h | Comp. Ex. 10 | Comp. Ex. 11 | Comp. Ex. 12 | Comp. Ex. 13 | Comp. Ex. 14 | Comp. Ex. 15 | Comp. Ex. 16 | Comp. Ex. 17 | Comp. Ex. 18 |
|---|---|---|---|---|---|---|---|---|---|
| 0 | 100 | 100 | 100 | 100 | 100 | 100 | 100 | 100 | 100 |
| 1 | 94.3 | 90.1 | 82.4 | 78.9 | 90.4 | 84.3 | 76.3 | 70.4 | 89.5 |
| 2 | 90.2 | 83.8 | 66.9 | 54.3 | 86.4 | 77.4 | 60.5 | 55.2 | 81.5 |
| 5 | 81.8 | 71.1 | 32.8 | 29.7 | 76.3 | 68.4 | 24.5 | 21.2 | 77.8 |
| 24 | 56 | 14.2 | N. D. | N. D. | 48.3 | 10.4 | N. D. | N. D. | 52.1 |

It can be seen from Table 4 that the compositions of Example 1 to 9 have higher stability in a glucomoringin, as compared to the compositions of Comparative Examples 10 to 18.

Test for Enhancing Action of Glutathione Production

The compositions of Examples 4 and 8 and Comparative Examples 4 and 8 were tested for enhancing action of glutathione production against B16 melanoma cells as follows.

B16 melanoma cells were pre-cultured using a 10% FBS-containing Dulbecco's MEM medium, and the cells were collected by trypsin treatment. The collected cells were diluted with a 10% FBS-containing Dulbecco's MEM medium so as to have a cell density of $10 \times 10^4$ cells/mL. Thereafter, the dilution was seeded to a 48-well plate in a volume of 200 μL each per well, and the cells were cultured overnight. After the culture, the medium was removed, and dissolved in a 1% FBS-containing Dulbecco's MEM medium so as to contain a moringin at the same concentration to provide a test sample. The test sample was added to each well in a volume of 200 μL, and the cells were cultured for 24 hours. Here, as the control, the cells were cultured in the same manner using a 1% FBS-containing Dulbecco's MEM medium without containing the sample. After the termination of culture, the medium was removed from each well, and the cells were washed with 400 μL of PBS(−) buffer, and the cells were then lysed using 150 μL of M-PER (manufactured by PIERCE).

A total glutathione was quantified using 100 μL of the solution. Specifically, 100 μL of a lysed cell extract, 50 μL of a 0.1 mmol/L phosphate buffer, 25 μL of 2 mmol/L NADPH and 25 μL of glutathione reductase (final concentration: 17.5 units/mL) were added to a 96-well plate, and warmed at 37° C. for 10 minutes. Thereafter, 25 μL of 10 mM 5,5'-dithiobis(2-nitrobenzoic acid) was added thereto, and the absorbance at a wavelength of 412 nm up to after 5 minutes was measured, to obtain ΔOD/min. A total glutathione concentration was calculated on the basis of a calibration curve drawn using oxidizing glutathione (manufactured by Wako Pure Chemical Industries, Ltd.). The value obtained was compensated to an amount of glutathione per total protein amount, and the enhancing rate of glutathione production, %, was calculated by the following formula. The results are shown in Table 5.

Enhancing Rate of Glutathione Production, $\% = A/B \times 100$, wherein A is an amount of glutathione per total protein amount in the cells added with the test sample; B is an amount of glutathione per total protein amount in the cells without adding the sample (control).

TABLE 5

|  | Enhancing Rate of Glutathione Production, % |
|---|---|
| Without addition of sample | 100 |
| Ex. 4 | 121.7 |
| Comp. Ex. 4 | 108.9 |
| Ex. 8 | 118.4 |
| Comp. Ex. 8 | 104.2 |

It can be seen from Table 5 that the compositions of Examples 4 and 8 have higher enhancing actions of glutathione production, as compared to the compositions of Comparative Examples 4 and 8.

Confirmation Test for Whitening Effects

Examples are shown regarding dermal agents for external applications containing a composition of each of Example 4 or 8 and Comparative Example 4 or 8 as an active ingredient. Method for producing a milky lotion: Ingredients 1 to 8 listed in Table 6 were heated to 80° C. to evenly dissolve or disperse the ingredients, to provide an oil phase. In addition, Ingredients 9, 10, and 12 were heated to 80° C., to provide an aqueous phase. The oil phase was added to the aqueous phase while stirring, and a preliminary emulsification was carried out. Thereafter, Ingredient 11 was added thereto, and the mixture was homogeneously emulsified with a homogenizing mixer. After the termination of emulsification, the emulsion was cooled, and each of the composition of Example 4 or 8 and Comparative Example 4 or 8 was added at 25° C. so as to contain a moringin at the same concentration, to provide a test sample. In addition, a sample in which a composition of Example 4 or 8 was replaced with purified water was provided as "without addition" of sample, and compared therewith.

In the confirmation test for whitening effects, the panelists were selected as 15 members per group, whose main symptoms were pigmentations such as blotches, freckles, and suntans of skins. Each group was asked to use the sample on faces and backside of hands in blind manner continuously for three months. The skin conditions before the beginning of the test used and that after the termination of the test used were photographed, and the changes in the state of pigmentations were judged by the specialized judging members in three ranks of "improved," "somewhat improved," and "no changes." The results are shown in Table 7.

TABLE 6

Table 6

|  | Ex 4 | Comp. Ex. 4 | Ex. 8 | Comp. Ex 8 | Without addition |
|---|---|---|---|---|---|
| ① Stearic acid, % by mass | 1 | 1 | 1 | 1 | 1 |
| ② Cetanol, % by mass | 1 | 1 | 1 | 1 | 1 |
| ③ Diisostearyl malate, % by mass | 3 | 3 | 3 | 3 | 3 |
| ④ Squalane, % by mass | 8 | 8 | 8 | 8 | 8 |
| ⑤ Cetyl 2-ethylhexanoate, % by mass | 8 | 8 | 8 | 8 | 8 |
| ⑥ Polyoxyethylene sorbitan monostearate, % by mass | 1.5 | 1.5 | 1.5 | 1.5 | 1.5 |
| ⑦ Glycerol monostearate, % by mass | 1.5 | 1.5 | 1.5 | 1.5 | 1.5 |
| ⑧ Cholesterol, % by mass | 0.2 | 0.2 | 0.2 | 0.2 | 0.2 |
| ⑨ 1% by mass aqueous solution of carboxyvinyl polymers, % by mass | 15 | 15 | 15 | 15 | 15 |
| ⑩ Dipropylene glycol, % by mass | 6 | 6 | 6 | 6 | 6 |
| ⑪ 10% by mass aqueous solution of L-arginine, % by mass | 1.5 | 1.5 | 1.5 | 1.5 | 1.5 |
| ⑫ Distilled water, % by mass | balance | balance | balance | balance | balance |
| Moringa extract and/or pulverized product (0.02% by mass in terms of moringin) | 1.96 | 1.26 | 5.23 | 2.75 | — |

TABLE 7

|  | Ex. 4 | Comp. Ex. 4 | Ex. 8 | Comp. Ex. 8 | Without addition |
|---|---|---|---|---|---|
| Improved | 11 | 4 | 11 | 3 | 0 |
| Somewhat improved | 3 | 5 | 2 | 4 | 0 |
| No changes | 1 | 6 | 2 | 8 | 15 |

It can be seen from Table 7 that the milky lotion containing a composition of Example 4 or 8 has higher whitening effects, as compared to the milky lotion containing a composition of Comparative Example 4 or 8 or the milky lotion containing purified water.

Lemon Beverages: Improvement in Bitterness of Glucomoringin

A lemon beverage containing a composition of each of Examples 1 to 4 and Comparative Examples 19 to 22 in an amount of 0.05% by mass in terms of the content of a glucomoringin, and sucralose in an amount of without addition, 0.005% by mass, or 0.014% by mass (pH 3, 0.08% by mass of citric acid, and 0.1% by mass of a lemon flavor (manufactured by T. HASEGAWA CO., LTD.), the pH being adjusted with trisodium citrate) was prepared.

The details of the ingredients are shown hereinbelow.

Sucralose: (manufactured by TATE & LYLE)

Evaluation of Bitterness

The sensory evaluation regarding the bitterness by a glucomoringin of a lemon beverage using a composition of each of Examples 1 to 4 and Comparative Examples 19 to 22 was made by seven panelists in a five-rank evaluation in accordance with the following criteria, and a mean score of total points was calculated. The results are shown in Table 8. The bitterness by a glucomoringin was subjected to sensory evaluations comprehensively of bitterness, stringency and unpleasant lingering taste (lingering bitter or stringent taste or the like) with the same ingredients, and each was relatively evaluated. In addition, a lemon beverage in which only a composition of each of Examples 1 to 4 and Comparative Examples 19 to 22 was added in an amount of 0.0005% (an amount 1/10 of the amount of each of Examples and Comparative Examples to a beverage) is defined as a rank 5.

(Evaluation Criteria)

1: Bitterness is the strongest among the same ingredients.

2: Bitterness is somewhat stronger but weaker than rank 1.

3: Bitterness is improved to a certain level as compared to rank 1.

4: Bitterness is improved as compared to rank 1.

5: Bitterness is highly improved as compared to rank 1.

TABLE 8

|  | Sucralose | | |
|---|---|---|---|
| Evaluation of Bitterness | Without Addition | 0.005% | 0.014% |
| Comp. Ex. 19 | 1.7 | 1.9 | 2.3 |
| Comp. Ex. 20 | 1.0 | 1.7 | 1.9 |
| Comp. Ex. 21 | 1.3 | 1.8 | 2.1 |
| Comp. Ex. 22 | 1.2 | 1.6 | 1.9 |
| Ex. 1 | 2.3 | 3.1 | 4.2 |
| Ex. 2 | 1.8 | 2.8 | 3.7 |
| Ex. 3 | 1.9 | 2.7 | 3.9 |
| Ex. 4 | 2.0 | 2.9 | 4.1 |

It can be seen from Table 8 that the lemon beverages containing compositions of Examples 1 to 4 are weak in bitterness, as compared to the lemon beverages containing compositions of Comparative Examples 19 to 22. Here, similar evaluations were also made with those containing 0.013% by mass or 0.04% by mass of aspartame (manufactured by AJINOMOTO CO., INC., PAL SWEET), 0.02% by mass or 0.05% by mass of acesulfame K (manufactured by Nutrinova, Sunnette), 0.02% by mass or 0.06% by mass of a Stevia extract (manufactured by Toyo Sugar Refining Co., Ltd., Stevilose 90), 3% by mass or 8% by mass of erythritol (manufactured by B Food Science Co., Ltd., Erythritol F), 3% by mass or 9% by mass of sorbitol (manufactured by B Food Science Co., Ltd., Sorbitol SP), 2% by mass or 6% by mass of xylitol (manufactured by B Food Science Co., Ltd., Xylitol), 0.03% by mass or 0.1% by mass of ascorbic acid (manufactured by FUSO CHEMICAL CO., LTD.), in place of 0.005% by mass or 0.014% by mass of sucralose. In addition, nearly the same results were shown with beverages having a content of a glucomoringin of 0.025% by mass.

Acidic Beverages: Improvement in Color Changes by Long-Term Storage of Glucomoringin An acidic beverage containing a composition of each of Examples 1 to 4 and Comparative Examples 19 to 22 in an amount of 0.05% by mass in terms of the content of a glucomoringin, and sucralose in an amount of without addition, 0.005% by mass, or 0.014% by mass (pH 3, 0.08% by mass of citric acid, the pH being adjusted with trisodium citrate) was prepared.

Evaluation of Colors

Colors of an acidic beverage using a composition of each of Examples 1 to 4 and Comparative Examples 19 to 22 immediately after the production and after a three-month storage at 37° C. were measured with a spectrophotometer (Cary60 UV-VIS, Software: CaryWinUV/Color, Agilent Technologies) by placing a sample in a quartz cell having an optical path length of 10 mm to measure a value of L, a value of a, and a value of b of the Lab color space. From the value of L, the value of a, and the value of b of an acidic beverage immediately after the production and the value of L, the value of a, and the value of b of an acidic beverage after a 3-month storage at 37° C., ΔE was obtained from the following formula, as shown in Table 9.

$$\Delta E = (\Delta L^2 + \Delta a^2 + \Delta b^2)^{0.5}$$

TABLE 9

| Evaluation of Colors | Sucralose | | |
|---|---|---|---|
| | Without Addition | 0.005% | 0.014% |
| Comp. Ex. 19 | 1.99 | 1.68 | 1.46 |
| Comp. Ex. 20 | 1.98 | 1.72 | 1.48 |
| Comp. Ex. 21 | 2.01 | 1.78 | 1.55 |
| Comp. Ex. 22 | 2.11 | 1.79 | 1.58 |
| Ex. 1 | 1.84 | 1.33 | 0.88 |
| Ex. 2 | 1.71 | 1.28 | 0.87 |
| Ex. 3 | 1.66 | 1.24 | 0.79 |
| Ex. 4 | 1.51 | 1.19 | 0.78 |

It can be seen from Table 9 that the acidic beverages containing compositions of Examples 1 to 4 have controlled color changes, as compared to the acidic beverages containing compositions of Comparative Examples 19 to 22. Here, similar evaluations were also made with those containing 0.013% by mass or 0.04% by mass of aspartame (manufactured by AJINOMOTO CO., INC., PAL SWEET), 0.02% by mass or 0.05% by mass of acesulfame K (manufactured by Nutrinova, Sunnette), 2% by mass or 6% by mass of a *Stevia* extract (manufactured by Toyo Sugar Refining Co., Ltd., Stevilose 90), 3% by mass or 8% by mass of erythritol (manufactured by B Food Science Co., Ltd., Erythritol F), 3% by mass or 9% by mass sorbitol (manufactured by B Food Science Co., Ltd., Sorbitol SP), 2% by mass or 6% by mass of xylitol (manufactured by B Food Science Co., Ltd., Xylitol), 0.03% by mass or 0.1% by mass of ascorbic acid (manufactured by FUSO CHEMICAL CO., LTD.), in place of 0.005% by mass or 0.014% by mass of sucralose. In addition, nearly the same results were shown with beverages having a content of a glucomoringin of 0.025% by mass.

Tablets: Improvements in Bitterness and Color Changes of Glucomoringin

A mixture of a composition of each of Examples 5 to 8 and Comparative Examples 23 to 26 in an amount of 1% by mass in terms of the content of a glucomoringin, sucralose in an amount of without addition, 0.04% by mass, or 0.2% by mass, 0.5% by mass of fine silicon dioxide particles, 2.5% by mass of citric acid, and a crystalline cellulose (balance) was each pressure-molded with a hydraulic pressing machine (manufactured by RIKEN SEIKO, and corresponding mortar and pestle at a pressure of 100 kg/cm', to produce a tablet having a diameter of 9 mm and a weight of 300 mg.

Evaluation of Bitterness

The sensory evaluation regarding the bitterness of a tablet using a composition of each of Examples 5 to 8 and Comparative Examples 23 to 26 was made by with five panelists, and a mean score of total points was calculated. The results are shown in Table 10. Tablets containing the same ingredients as those of the lemon beverages were compared, and evaluated on the basis of the same evaluation criteria as those of the lemon beverages. Here, the tablets were evaluated for bitterness when two tablets were chewed up and swallowed.

Evaluation of Colors

Values of Lab of a tablet using a composition of each of Examples 5 to 8 and Comparative Examples 23 to 26 immediately after the production and after a three-month storage at 37° C. were measured, and ΔE values calculated are shown in Table 11. Specifically, as the values of Lab, those tablets crushed with a mortar were dissolved in an acidic solution (pH 3.1, 0.08% of citric acid, being adjusted with trisodium citrate) so as to have the content of a glucomoringin of 0.05% by mass or a converted value thereof, and filtered, and the values of Lab were then measured. The measurement method and the calculation method for ΔE values are the same as those for the acidic beverages.

TABLE 10

| Evaluation of Bitterness | Sucralose | | |
|---|---|---|---|
| | Without Addition | 0.005% | 0.014% |
| Comp. Ex. 23 | 1.7 | 2.0 | 2.4 |
| Comp. Ex. 24 | 1.6 | 1.9 | 2.3 |
| Comp. Ex. 25 | 1.0 | 1.7 | 1.9 |
| Comp. Ex. 26 | 1.6 | 1.7 | 2.1 |
| Ex. 5 | 1.8 | 2.8 | 3.3 |
| Ex. 6 | 1.9 | 2.9 | 3.9 |
| Ex. 7 | 1.9 | 3.1 | 3.9 |
| Ex. 8 | 2.1 | 3.4 | 4.2 |

TABLE 11

| Evaluation of Colors | Sucralose | | |
|---|---|---|---|
| | Without Addition | 0.040% | 0.2% |
| Comp. Ex. 23 | 1.52 | 1.25 | 1.19 |
| Comp. Ex. 24 | 1.56 | 1.38 | 1.29 |
| Comp. Ex. 25 | 1.42 | 1.36 | 1.21 |
| Comp. Ex. 26 | 1.41 | 1.33 | 1.27 |
| Ex. 5 | 1.31 | 0.91 | 0.77 |
| Ex. 6 | 1.29 | 0.90 | 0.71 |
| Ex. 7 | 1.26 | 0.86 | 0.69 |
| Ex. 8 | 1.13 | 0.81 | 0.66 |

It can be seen from Tables 10 and 11 that the tablets containing a composition of each of Examples 5 to 8 are weaker in bitterness and have controlled color changes, as compared to the tablets containing a composition of each of Comparative Examples 23 to 26. Here, similar evaluations were also made with those containing 0.1% by mass or 0.5% by mass of aspartame (manufactured by AJINOMOTO CO., INC., PAL SWEET), 0.14% by mass or 0.7% by mass of acesulfame K (manufactured by Nutrinova, Sunnette), 0.08% by mass or 0.2% by mass of a *stevia* extract (manufactured by Toyo Sugar Refining Co., Ltd., Stevilose 90), 14% by mass or 70% by mass of erythritol (manufactured by B Food Science Co., Ltd., Erythritol F), 14% by mass or 70% by mass sorbitol (manufactured by B Food Science Co., Ltd., Sorbitol SP), 14% by mass or 70% by mass of xylitol (manufactured by B Food Science Co., Ltd., Xylitol), 0.2% by mass or 1% by mass of ascorbic acid (manufactured by FUSO CHEMICAL CO., LTD.), in place of 0.04% by mass or 0.2% by mass of sucralose. In addition, nearly the same results were shown with tablets having a content of a glucomoringin of 0.025% by mass.

Black Tea Beverages: Improvements in Pungency and Unpleasant Odor of Moringin

Raw materials as listed in Table 12 were stir-mixed using a composition of each of Examples 3 and 4 and Comparative Examples 3 and 4, and the mixture was then subjected to a total volume compensation, a flavor was added when the temperature reached at 93° C., and the mixture was subjected to hot-pack filling in a 350 mL PET bottle, to prepare a black tea beverage (pH 5). The details of the ingredients as listed in Table 12 are shown hereinbelow.

Black tea extract: A black tea concentrate (manufactured by GS FOOD CO., LTD.)
Sodium hydrogencarbonate: (manufactured by Taiyo Pharmaceutical Co., LTD.)
*Stevia* extract: (manufactured by Toyo Sugar Refining Co., Ltd., Stevilose 90)
L-Ascorbic acid: (manufactured by FUSO CHEMICAL CO., LTD.)
Xylitol: (manufactured by B Food Science Co., Ltd.)
Black tea flavor: (manufactured by OGAWA Flavors & Flagrances Co., Ltd.)

Evaluations of Pungency and Unpleasant Odor

The sensory evaluation of a black tea beverage using a composition of each of Examples 3 and 4 and Comparative Examples 3 and 4 regarding the pungency and the unpleasant odor was made by seven panelists in a three-rank evaluation in accordance with the following criteria, and a mean score of total points was calculated. The pungency and the unpleasant odor were subjected sensory evaluations comprehensively, and compared. Since a black tea beverage of Comparative Example 4 containing only a moringin had the strongest pungency and unpleasant odor, the evaluation thereof is defined as 1, and the evaluation in which the amount of Comparative Example 4 was adjusted to a factor of ⅟₅₀ is defined as 3.

The results are shown in Table 12.
(Evaluation Criteria)
1: Pungency and unpleasant odor are strongest.
2: Pungency and unpleasant odor are improved more than those of the evaluation 1.
3: Pungency and unpleasant odor are highly improved than those of the evaluation 1.

TABLE 12

|  | Ex. 3 | Ex. 4 | Comp. Ex. 3 | Comp. Ex. 4 |
|---|---|---|---|---|
| Black tea extract, % by mass | 18.6 | 18.6 | 18.6 | 18.6 |
| Sodium hydrogencarbonate, % by mass | 0.002 | 0.002 | 0.002 | 0.002 |
| Moringa extract, 0.01% by mass in terms of moringin | 2.95 | 0.98 | 0.76 | 0.63 |
| Stevia extract, % by mass | 0.03 | 0.03 | 0.03 | 0.03 |
| L-Ascorbic acid, % by mass | 0.03 | 0.03 | 0.03 | 0.03 |
| Xylitol, % by mass | 6 | 6 | 6 | 6 |
| Black tea flavor, % by mass | 0.1 | 0.1 | 0.1 | 0.1 |
| Distilled water, % by mass | balance | balance | balance | balance |
| Total amount, % by mass | 100 | 100 | 100 | 100 |
| Evaluations of Pungency and Unpleasant Odor | 2.6 | 2.1 | 1.1 | 1.0 |

It can be seen from Table 12 that the black tea beverages containing a composition of each of Examples 3 and 4 have controlled pungency and unpleasant odor, as compared to the black tea beverages containing a composition of each of Comparative Examples 3 and 4.

Coffee Beverages: Improvements in Pungency and Unpleasant Odor of Moringin

Raw materials as listed in Table 13 using a composition of each of Examples 3 and 4 and Comparative Examples 3 and 4 were stir-mixed, and the mixture was then subjected to a total volume compensation. The mixture was then homogenized with a homogenizer when the temperature reached at 70° C. Thereafter, a 200 mL canister was subjected to retort-sterilization at 121° C. for 15 minutes, to prepare a coffee beverage. The evaluations of pungency and unpleasant order were made in the same manner as in the black tea beverages. The results are shown in Table 13. Here, the evaluation criteria were the same criteria as those of the black tea beverages.

The details of the ingredients as listed in Table 13 are shown hereinbelow.
Coffee extract: (manufactured by GS FOOD CO., LTD.)
Cow's milk: (manufactured by Meiji Dairies Co., Ltd.)
Skim milk powder: (manufactured by Yotsuba Milk Products Co., Ltd.)
Sugar: (manufactured by Mitsui Sugar Co., Ltd.)
Emulsifier: (manufactured by Taiyo Kagaku Co., Ltd.)
Sodium hydrogencarbonate: (manufactured by Taiyo Pharmaceutical Co., LTD.)
Coffee flavor: (OGAWA Flavors & Flagrances Co., Ltd.)
Sucralose: (manufactured by TATE & LYLE)
Erythritol: (manufactured by B Food Science Co., Ltd.)

TABLE 13

|  | Ex. 3 | Ex. 4 | Comp. Ex. 3 | Comp. Ex. 4 |
|---|---|---|---|---|
| Coffee extract, % by mass | 32.6 | 32.6 | 32.6 | 32.6 |
| Cow's milk, % by mass | 21 | 21 | 21 | 21 |
| Skim milk powder, % by mass | 0.1 | 0.1 | 0.1 | 0.1 |
| Whole milk powder | 0.1 | 0.1 | 0.1 | 0.1 |
| Sugar, % by mass | 6 | 6 | 6 | 6 |
| Emulsifier, % by mass | 0.18 | 0.18 | 0.18 | 0.18 |
| Sodium hydrogencarbonate, % by mass | 0.12 | 0.12 | 0.12 | 0.12 |
| Moringa extract, 0.02% by mass in terms of moringin | 5.91 | 1.96 | 1.52 | 1.26 |
| Coffee flavor, % by mass | 0.06 | 0.06 | 0.06 | 0.06 |
| Sucralose, % by mass | 0.014 | 0.014 | 0.014 | 0.014 |
| Erythritol, % by mass | 3 | 3 | 3 | 3 |
| Distilled water, % by mass | balance | balance | balance | balance |
| Total amount, % by mass | 100 | 100 | 100 | 100 |
| Evaluations of pungency and unpleasant odor | 2.7 | 2.5 | 1.6 | 1.0 |

It can be seen from Table 13 that the coffee beverages containing a composition of each of Examples 3 and 4 have controlled pungency and unpleasant odor, as compared to the coffee beverages containing a composition of each of Comparative Examples 3 and 4.

Granules: Improvements in Pungency and Unpleasant Odor of Moringin

Dextrose monohydrate, sucralose, and a composition of each of Examples 7 and 8 and Comparative Examples 7 and 8 were powder-blended, and the remaining raw materials as listed in Table 14 were then mixed therewith, while stir-mixing the components with a mixing agitator. After the mixing, the mixture was dried at 60° C. for 2 hours with a hot-air dryer, to produce granules. The evaluations of pungency and unpleasant odor were made in the same manner as in the black tea beverages. The results are shown in Table 14. Since the granules of Comparative Example 8 having the highest parts by mass of the moringin had the most intensive pungency and unpleasant odor, the evaluation thereof is defined as 1, the evaluation in which the amount in Comparative Example 8 was adjusted to a factor of 1/50 is defined as 3.

The details of the ingredients as listed in Table 14 are shown hereinbelow.
Green tea powder: (manufactured by ITO EN, LTD.)
Green tea flavor: (manufactured by OGAWA Flavors & Flagrances Co., Ltd.)
Sucralose: (manufactured by TATE & LYLE)
Dextrose monohydrate: (manufactured by San-ei Sucrochemical Co., Ltd.)

TABLE 14

|  | Ex. 7 | Ex. 8 | Comp. Ex. 7 | Comp. Ex. 8 |
|---|---|---|---|---|
| Green tea powder, % by mass | 3 | 3 | 3 | 3 |
| Distilled water, % by mass | 5 | 5 | 5 | 5 |
| Green tea flavor, % by mass | 1 | 1 | 1 | 1 |
| Moringa pulverized product, 0.1% by mass in terms of moringin | 56.49 | 26.17 | 17.63 | 13.77 |
| Sucralose, % by mass | 0.015 | 0.015 | 0.015 | 0.015 |
| Dextrose monohydrate, % by mass | balance | balance | balance | balance |
| Total amount, % by mass | 100 | 100 | 100 | 100 |
| Evaluations of pungency and unpleasant odor | 2.4 | 2.4 | 1.5 | 1.0 |

It can be seen from Table 14 that the granules containing a composition of each of Examples 7 and 8 have controlled pungency and unpleasant odor, as compared to the granules containing a composition of each of Comparative Examples 7 and 8.

Confirmation Test for Anti-Fatigue Effects

Six-week old male SD rats (n=10) were bred at room temperature of 23°±2° C., feeding with a standard feed and water for a week to allow conditioning. Next, the rats of which conditioning was terminated were subjected to forcible swimming under application of a load (see below), and a swimming time (seconds) until the rats were drown was measured. The rats were divided into three groups by assigning the rats evenly as much as possible, on the bases of the results of the swimming time so that the mean of the swimming time of each group would be the same in each group. As the method for administering each composition, the rats which were assigned to the groups were administered with water, a composition of Example 4 or a composition of Comparative Example 4 at a frequency of once a day (at 8:00 to 12:00) for 4 weeks. As to the composition of each of Example 4 and Comparative Example 4, the composition was dissolved so as to have the same amount in terms of a glucomoringin concentration, and the solution was forcibly orally administered at 2 mg/kg body weight in terms of glucomoringin. Here, as to the moringin contained in the composition of each of Example 4 and Comparative Example 4 at dissolution, a converted content to a glucomoringin was calculated using the conversion formula from a moringin to a glucomoringin shown in the analysis conditions mentioned above, and the concentration was adjusted in terms of the content of a glucomoringin.

Forcible Swimming Under Application of Load

Figure 3:
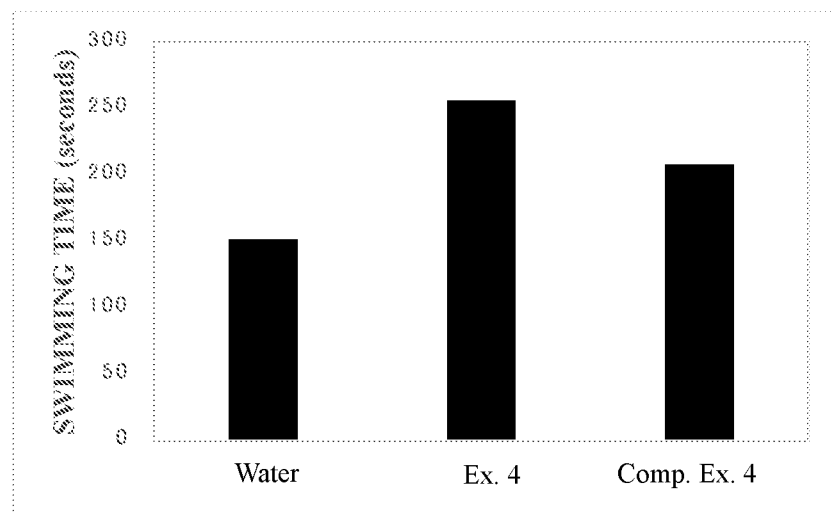
FIG. 3 A graph showing a swimming time of rats given with Example 4 and Comparative Example 4.

On the day of grouping and 2 hours after the administration of the fourth week of administration of each composition, a weight corresponding to 5% of the body weight was attached to the hypogastrium of the rats, and the rats were placed in a cylinder to allow swimming. The time (seconds) until the rats were drown was measured, which is defined as a swimming time. When mouths and noses of the rats were submerged continuously for 10 seconds during the swimming, it was judged that the rats were drowned. It can be seen from FIG. 3 that the composition of Example 4 has an increased swimming time at a low dosage in terms of the converted content of a glucomoringin, as compared to the composition of Comparative Example 4.

INDUSTRIAL APPLICABILITY

The composition of the present invention is useful in the fields of foodstuff, cosmetics, and the like.

The invention claimed is:
1. A composition comprising a *Moringa* extract and/or a *Moringa* pulverized product, wherein a mass ratio of a content of a moringin to a content of a glucomoringin (moringin/glucomoringin) is from 0.00005 to 0.30, wherein a myrosinase is deactivated, or the composition does not comprise a myrosinase, and wherein the content of a glucomoringin is 1.5% by mass or more calculated in terms of a dry solid content.

2. Foodstuff comprising a composition as defined in claim 1.

3. Cosmetics comprising a composition as defined in claim 1.

* * * * *